United States Patent
Liu et al.

(10) Patent No.: US 8,626,315 B2
(45) Date of Patent: Jan. 7, 2014

(54) ELECTRONIC PACEMAKER AND PACEMAKER ELECTRODE

(75) Inventors: Kai Liu, Beijing (CN); Li Fan, Beijing (CN); Wen-Mei Zhao, Beijing (CN); Ying-Hui Sun, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 0 days.

(21) Appl. No.: 13/096,200

(22) Filed: Apr. 28, 2011

(65) Prior Publication Data

US 2012/0053649 A1 Mar. 1, 2012

(30) Foreign Application Priority Data

Aug. 31, 2010 (CN) .......................... 2010 1 0268024

(51) Int. Cl.
*A61N 1/00* (2006.01)
(52) U.S. Cl.
USPC ......................................................... 607/119
(58) Field of Classification Search
USPC ................................................ 607/119–156
See application file for complete search history.

(56) References Cited

U.S. PATENT DOCUMENTS

| 7,894,914 B2 * | 2/2011 | Stahmann et al. ............ 607/119 |
| 2007/0293086 A1 | 12/2007 | Liu et al. |
| 2008/0161886 A1 | 7/2008 | Stevenson et al. |
| 2009/0202764 A1 * | 8/2009 | Tonon et al. ................. 428/36.3 |
| 2009/0255706 A1 | 10/2009 | Jiang et al. |
| 2010/0076536 A1 | 3/2010 | Merz et al. |

FOREIGN PATENT DOCUMENTS

| CN | 2734251 | 10/2005 |
| CN | 101090011 | 12/2007 |
| CN | 101508420 A | 8/2009 |
| JP | 2010504128 | 2/2012 |
| TW | 200945372 | 11/2009 |
| WO | WO2009065171 | 5/2009 |

\* cited by examiner

*Primary Examiner* — Christopher D Koharski
*Assistant Examiner* — Nadia Ahmad
(74) *Attorney, Agent, or Firm* — Altis Law Group, Inc.

(57) ABSTRACT

A pacemaker includes a pulse generator, a conduction line, and a pacemaker electrode. The pacemaker electrode includes a body and an insulation layer. The body includes at least one carbon nanotube yarn. The carbon nanotube yarn includes a number of carbon nanotubes. The carbon nanotubes are interconnected along one axis of the body by van der Waals force. The insulation layer covers an outer surface of the body.

20 Claims, 8 Drawing Sheets

ELECTRONIC PACEMAKER AND PACEMAKER ELECTRODE

BACKGROUND

1. Technical Field

The present application is related to electronic pacemakers, and more particularly to a brain pacemaker and a pacemaker electrode which are using carbon nanotube.

2. Description of Related Art

Parkinson's disease (PD) is a degenerative disorder of the central nervous system that impairs motor skills, cognitive processes, and other functions. PD is the most common cause of chronic progressive syndrome characterized by tremor, rigidity, bradykinesia and postural instability.

Deep brain stimulation (DBS) is presently the most used surgical means of treatment but other surgical therapies consisting of producing lesions in specific subcortical areas are also effective. DBS involves the implantation of a medical device called a brain pacemaker, which sends electrical impulses to specific parts of the brain.

BRIEF DESCRIPTION OF THE DRAWINGS

The parts in the drawings are not necessarily drawn to scale, the emphasis instead being placed upon clearly illustrating the principles of at least one embodiment. In the drawings, like reference numerals designate corresponding parts throughout the various diagrams, and all the diagrams are schematic.

DETAILED DESCRIPTION

Reference will now be made to the drawings to describe various inventive embodiments of the present disclosure in detail, wherein like numerals refer to like elements throughout.

Figure 1:
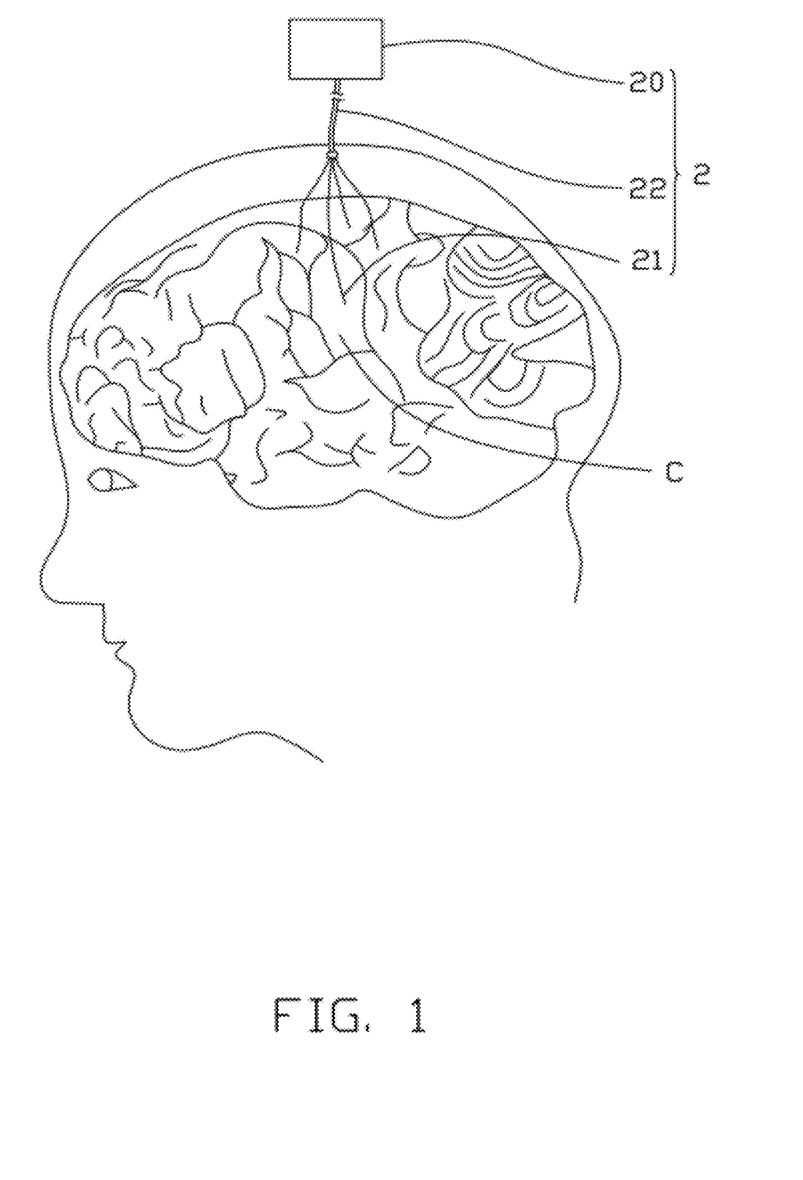
FIG. 1 is a diagram of an electronic pacemaker according to one embodiment of the disclosure.

Referring to FIG. 1, a pacemaker 2, which can be a brain pacemaker or a cardiac pacemaker, according to the embodiment of the disclosure includes a pulse generator 20, a pacemaker electrode 21, and a conduction line 22. The conduction line 22 is electrically connected between the pulse generator 20 and the pacemaker electrode 21. The pulse generator 20 generates an electrical pulse signal traveling through the conduction line 22 and the pacemaker electrode 21.

The pulse generator 20 includes a shell, a power source, an electrical pulse generating circuit, a control circuit, and an interface. The shell can be made of titanium to protect the internal components. In one embodiment, the power source powers the pulse generator. The electrical pulse generating circuit generates electrical pulse signals. The control circuit controls the electrical pulse generating circuit to generate different electrical pulse signals with different signal levels. The interface is electrically connected to the conduction line 22. The electrical pulse signal generated by the pulse generator is transmitted to the brain via the conduction line 22 and the pacemaker electrode 21 to stimulate the target cell or cells of the brain, for example, the cerebral cell C (shown in FIG. 1).

Figure 2:
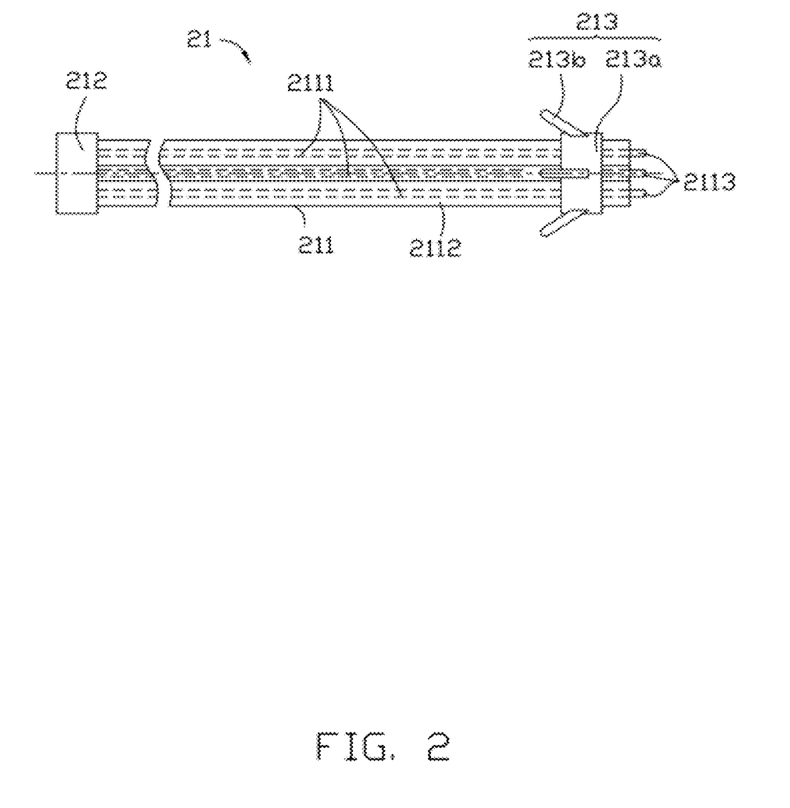
FIG. 2 is a diagram of a pacemaker electrode of FIG. 1.
Figure 3:
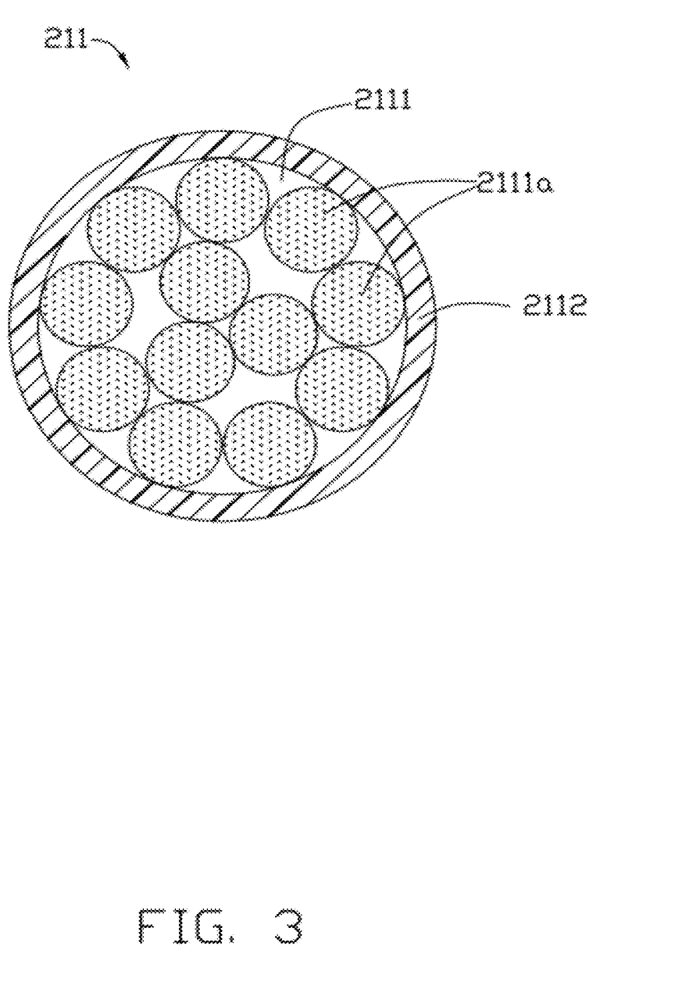
FIG. 3 is a cross-section of the pacemaker electrode of FIG. 2.

Referring to FIG. 2 and FIG. 3, the pacemaker electrode 21 according to one embodiment includes at least one electrode line 211, a connecting terminal 212, and a fixing member 213. The connecting terminal 212 and the fixing member 213 are disposed at different ends of the electrode line 211. The connecting terminal 212 can be an externally threaded cylinder made of platinum or platinum-iridium alloy. The diameter of the connecting terminal 212 is in the range of 1 mm to 3 mm. The connecting terminal 212 can be fixed inside the human body, for example, in the skull. The electrode line 211 can be electrically connected to the conduction line 22 through the connecting terminal 212. The fixing member 213 is fixed on the exterior of the electrode line 211 and inserted into the human body for fixing the pacemaker electrode 21. In another embodiment, the pacemaker electrode 21 has a plurality of electrode lines 211 tightly contacting each other in parallel to form a bundle structure. The connection terminal 212 and the fixing member 213 are located at two ends of the bundle structure.

The fixing member 213 includes a fixing ring 213a and a plurality of fixing wings 213b, which can be made of high polymer material like polyurethane or silicone elastomer. The fixing ring 213a can have a cylindrical structure. The fixing wings 213b can have a claviform structure extending along a direction from the outer surface of the fixing ring 213a to the central axis of the fixing ring 213a. An angle between the axis of the claviform structure and a central axis of the fixing ring 213a can be in the range from about 30 degrees to about 60 degrees. The fixing wing 213b can be wrapped with human tissue after the fixing member 213 is implanted into the human body to fix the pacemaker electrode 21 in place.

The electrode line 211 has a body 2111 and an insulation layer 2112. The insulation layer 2112 covers an outer surface of the body 2111. An end of the body 2111 has an exposed portion 2113 exposed from the insulation layer 2112. A length of the exposed portion is in the range from about 0.5 mm to about 2 mm. The exposed portion is a stimulus point for transmitting the electrical pulse signal generated by the pulse generator 20 to the target cell or cells of the human body.

The fixing member 213 is disposed at the end of the electrode line 211 near the exposed portion 2113. The distance between the exposed portion 2113 and the fixing member 213 is in the range from about 3 mm to about 5 mm. The insulation layer 2112 is made of polymer material like polyurethane or silicon elastomer. The thickness of the insulation layer 2112 is in the range from 1 μm to 50 μm.

The body 2111 includes at least one carbon nanotube yarn 2111a. The diameter of the carbon nanotube yarn 2111a is in the range from about 1 μm to about 200 μm and the diameter of the body 2111 is in the range from about 1 μm to about 2 mm. In one embodiment, the diameter of the body 2111 is in the range from about 1 μm to about 10 μm. The carbon nanotube yarn 2111a can be non-twisted carbon nanotube yarn or twisted carbon nanotube yarn.

Figure 4:
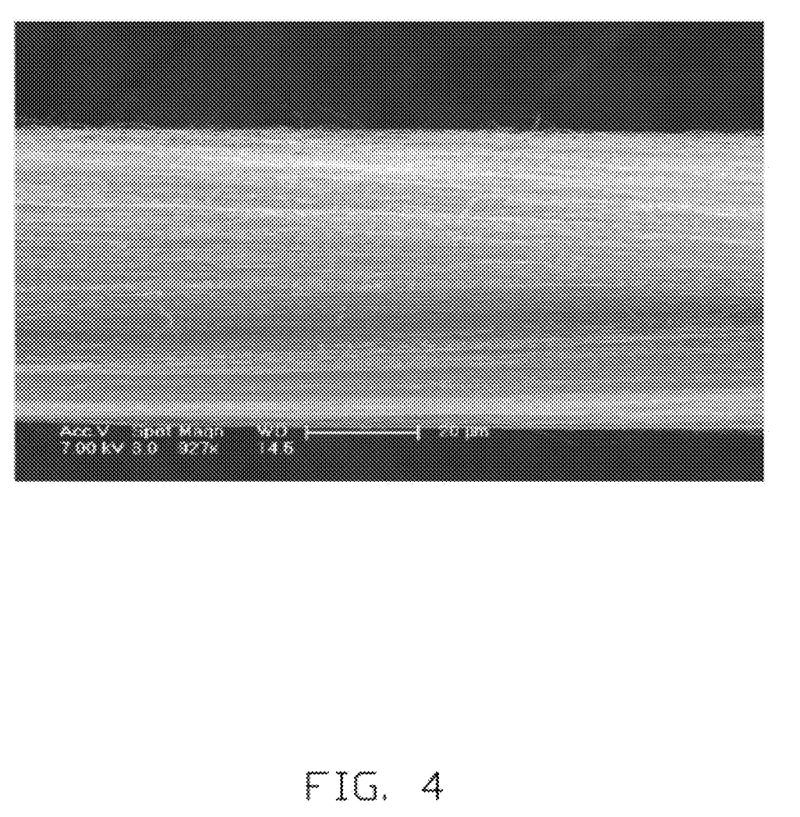
FIG. 4 is a picture taken by electron microscope of a non-twisted carbon nanotube yarn.

Referring to FIG. 4, the non-twisted carbon nanotube yarn includes a plurality of carbon nanotubes interconnected along an axial direction of the carbon nanotube yarn. The non-twisted carbon nanotube yarn includes a plurality of carbon nanotube segments interconnected by van der Waals force. Each carbon nanotube segment includes a plurality of carbon nanotubes interconnected in parallel by van der Waals force. The carbon nanotubes can be single-walled carbon nanotubes, dual-walled carbon nanotubes, or multi-walled carbon nanotubes.

Figure 5:
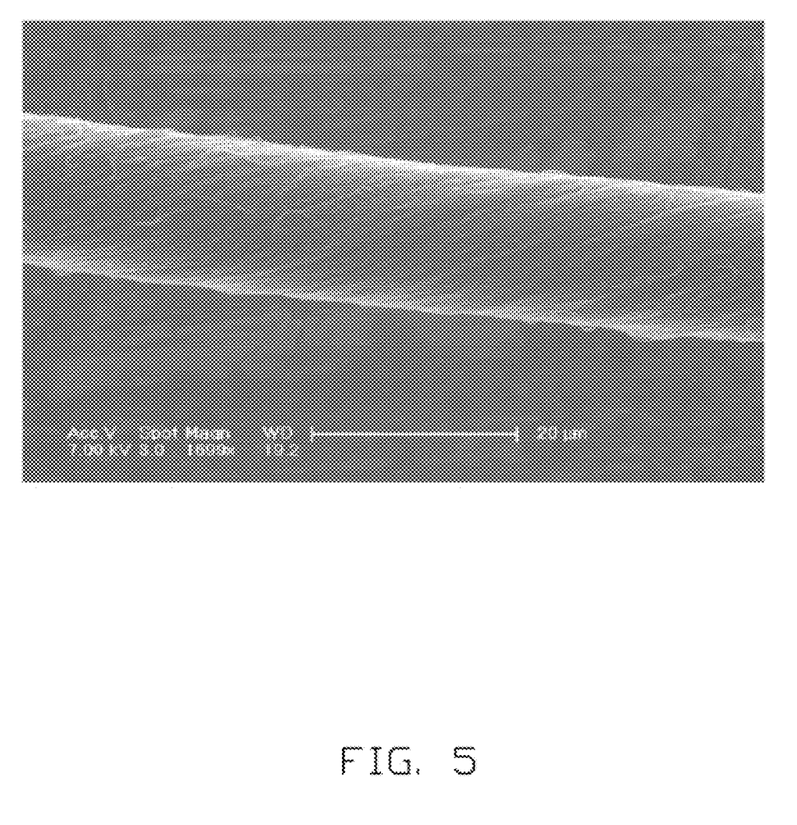
FIG. 5 is a picture taken by electron microscope of a twisted carbon nanotube yarn.

Referring to FIG. 5, the twisted carbon nanotube yarn includes a plurality of carbon nanotubes extending in a spiral along an axis of the carbon nanotube yarn. The twisted carbon nanotube yarn includes a plurality of carbon nanotube segments interconnected by van der Waals force. Each carbon nanotube segment includes a plurality of carbon nanotubes interconnected in parallel by van der Waals force. The carbon nanotubes can be single-walled carbon nanotubes, dual-walled carbon nanotubes, or multi-walled carbon nanotubes.

Figure 6:
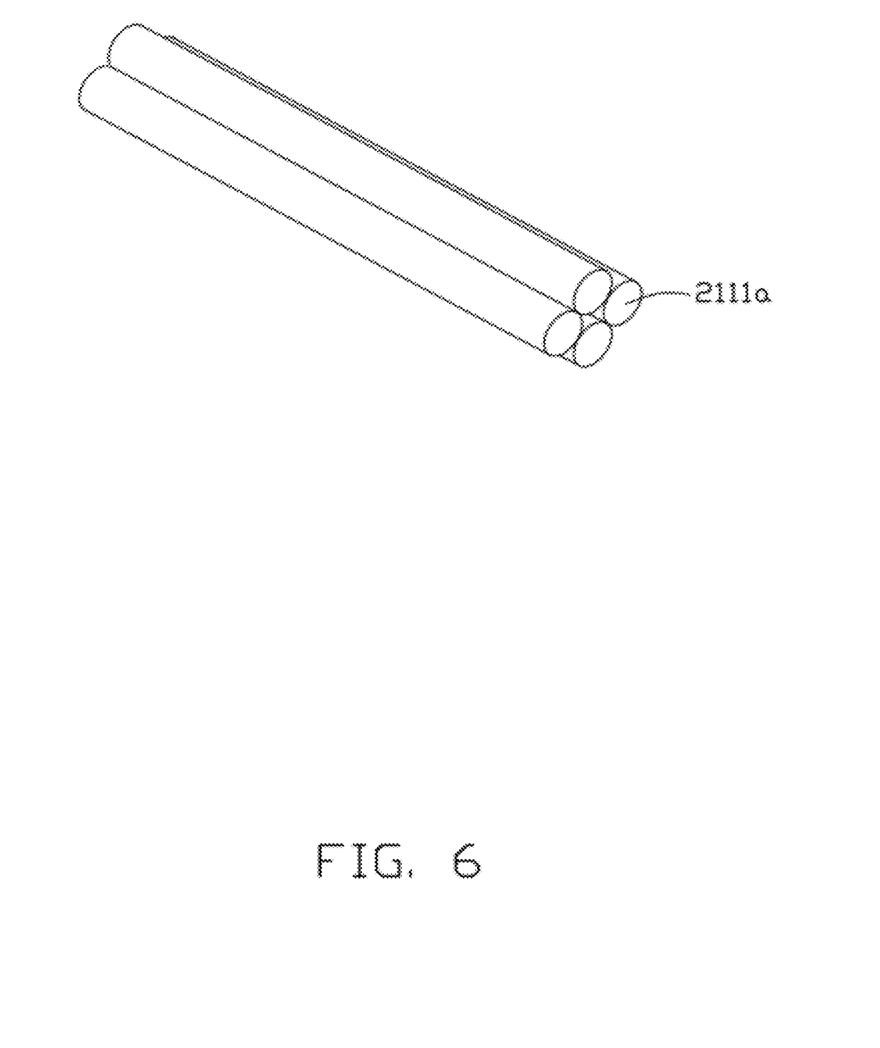
FIG. 6 is a diagram of a plurality of carbon nanotube yarns arranged in tight contact with each other to form a bundle structure.
Figure 7:
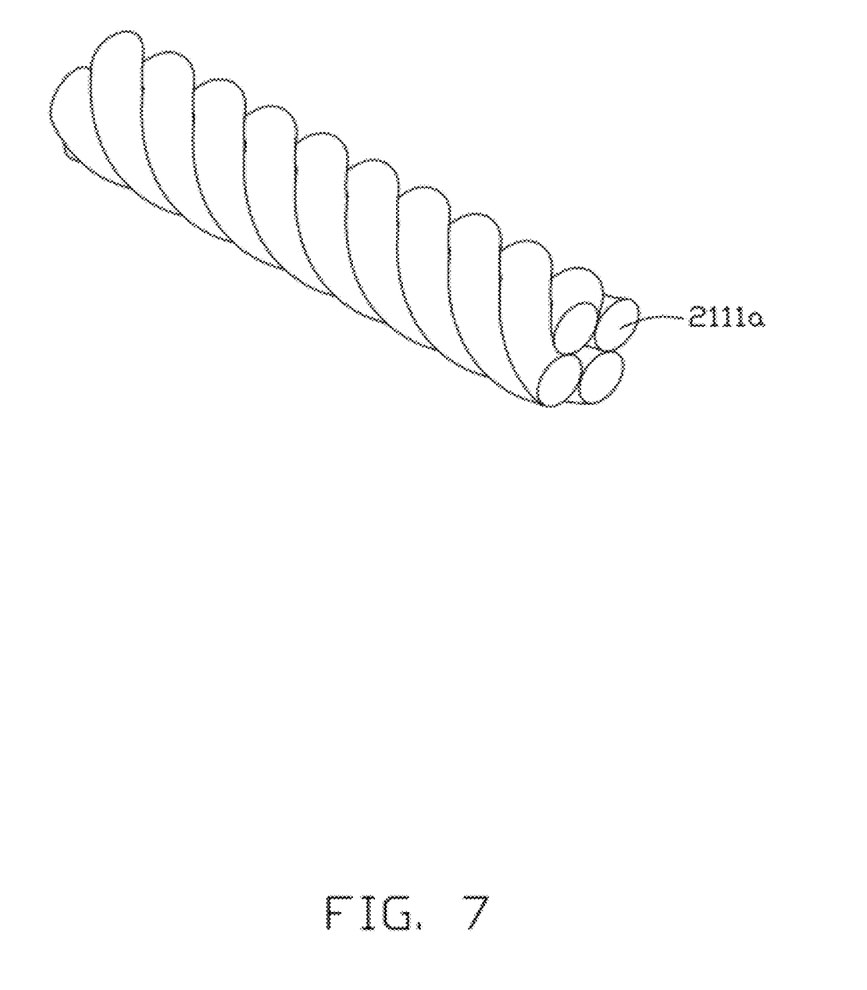
FIG. 7 is a diagram of a plurality of carbon nanotube yarns wound to form a bundle structure.

Referring to FIG. 6 and FIG. 7, in another embodiment, the body 2111 includes a plurality of carbon nanotube yarns 2111a, which are arranged tightly contacting each other in parallel or wound to form a bundle structure. FIG. 6 is a diagram of the body 2111 with the carbon nanotube yarns 2111a arranged tight contacting each other in parallel to form the bundle structure. FIG. 7 is a diagram of the body 2111 with the carbon nanotube yarns 2111a wound around the axis of the pacemaker electrode 21 at zero pitch to form the bundle structure.

Figure 8:
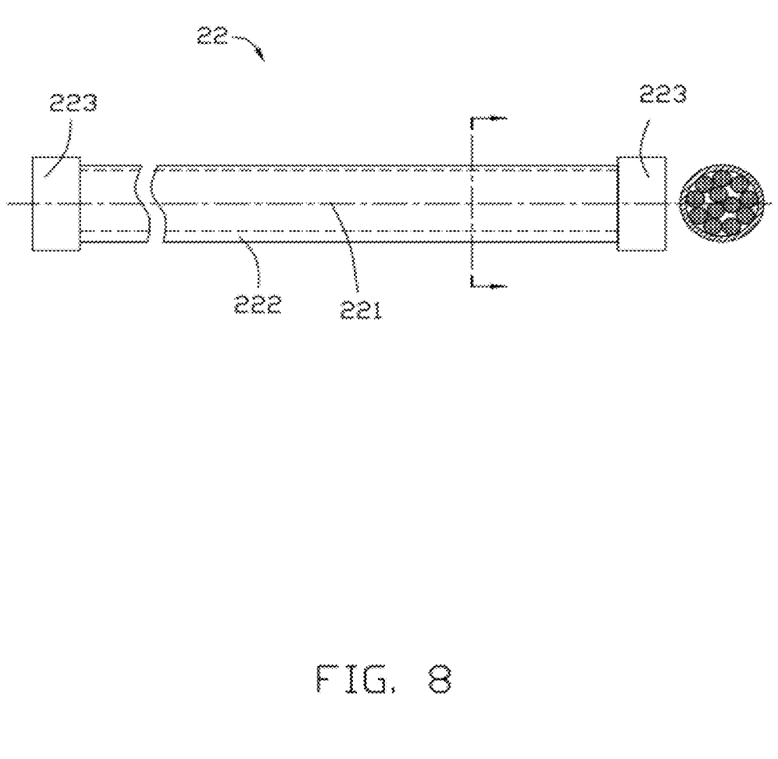
FIG. 8 is a diagram of a pacemaker conduction line according to the embodiment of FIG. 1.

Referring to FIG. 8, in the embodiment, the conduction line 22 includes a line core 221 and an insulation layer 222. The insulation layer 222 covers an outer surface of the line core 221. The characteristics of the insulation layer 222 are the same as the characteristics of the insulation layer 2112 of the electrode line 211. The conduction line 22 includes two connection terminals 223 located at two ends of the conduction line 22 respectively. The line core 221 can be a metal line such as a platinum line or a platinum-iridium alloy line. In another embodiment, the structure and the material of the line core 221 of the conduction line 22 may be the same as the body 2111 of the electrode line 211. The conduction terminal 223 can have a hollow cylindrical structure and be internally threaded. The diameter, thread count, and pitch of the conduction terminal 223 match the thread of the conduction terminal 212 of the pacemaker electrode 21. The two conduction terminals 223 are electrically connected to the conduction line 22. One of the conduction terminals is electrically connected to the pulse generator 20 and another of the conduction terminals is electrically connected to the conduction terminal 212 of the pacemaker electrode 21 so that the pulse generator 20, conduction line 22, and the pacemaker electrode 21 are electrically connected in series.

In the embodiment, the conduction line 22 and the pacemaker electrode 21 can be integrally formed. The diameter of the integral structure may be less than 10 μm. In addition, one conduction line 22 can be connected to a plurality of pacemaker electrode 21 through the conduction terminal 223. The carbon nanotube structures describe herein can be used in a similar manner for corresponding parts in other kinds of pacemakers such as artificial pacemakers used for the heart.

It is to be understood, however, that even though numerous characteristics and advantages of certain inventive embodiments have been set out in the foregoing description, together with details of the structures and functions of the embodiments, the disclosure is illustrative only; and that changes may be made in detail, especially in matters of arrangement of parts within the principles of the present disclosure to the full extent indicated by the broad general meaning of the terms in which the appended claims are expressed.

What is claimed is:

1. A pacemaker electrode comprising at least one electrode line, the at least one electrode line comprising: a body and an insulation layer covering a surface of the body, the body having an end exposed from the insulation layer,
   wherein the body comprises at least one carbon nanotube yarn, the at least one carbon nanotube yarn comprises a plurality of carbon nanotubes interconnected along an axis of the body by van der Waals force, one end of the at least one carbon nanotube yarn is exposed from the insulation layer, the exposed at least one carbon nanotube yarn is a stimulus point and configured to transmit an electrical pulse signal to a target cell or target cells of human body.

2. The pacemaker electrode of claim 1, wherein the plurality of carbon nanotubes extend along an axis of the at least one carbon nanotube yarn.

3. The pacemaker electrode of claim 1, wherein the plurality of carbon nanotubes extend in a spiral along an axis of the at least one carbon nanotube yarn.

4. The pacemaker electrode of claim 1, wherein a diameter of the at least one carbon nanotube yarn is in the range from about 1 μm to about 200 μm.

5. The pacemaker electrode of claim 1, wherein a diameter of the body is in a range from about 1 μm to about 2 mm.

6. The pacemaker electrode of claim 5, wherein the diameter of the body is in the range from about 1 μm to about 10 μm.

7. The pacemaker electrode of claim 1, wherein the at least one electrode line comprises a plurality of electrode lines tightly contacting each other in parallel.

8. The pacemaker electrode of claim 1, wherein the body comprises at least two carbon nanotube yarns arranged tightly contacting each other in parallel to form a bundle structure.

9. The pacemaker electrode of claim 1, wherein the body comprises at least two carbon nanotube yarns wound to form a bundle structure.

10. The pacemaker electrode of claim 1, wherein a thickness of the insulation layer is in the range from about 1 μm to about 50 μm.

11. A pacemaker, comprising:
    a pulse generator;
    a conduction line electrically connected with the pulse generator; and
    a pacemaker electrode comprising at least one electrode line the at least one electrode line comprising: a body and an insulation layer covering a surface of the body, the body having an end exposed from the insulation layer,
    wherein the body comprises at least one carbon nanotube yarn, the at least one carbon nanotube yarn comprises a plurality of carbon nanotubes interconnected along an axis of the body by van der Waals force, one end of the at least one carbon nanotube yarn is exposed from the insulation layer, the exposed at least one carbon nanotube yarn is a stimulus point and configured to transmit an electrical pulse signal to a target cell or target cells of human body.

12. The pacemaker of claim 11, wherein the plurality of carbon nanotubes extend along an axis of the at least one carbon nanotube yarn.

13. The pacemaker of claim 11, wherein the plurality of carbon nanotubes extend in a spiral along an axis of the at least one carbon nanotube yarn.

14. The pacemaker of claim 11, wherein the pacemaker electrode comprises at least two carbon nanotube yarns, the at least two carbon nanotube yarns are arranged tightly contacting each other in parallel to form a bundle structure.

15. The pacemaker of claim 11, wherein the pacemaker electrode comprises at least two carbon nanotube yarns, the at least two carbon nanotube yarns are wound to form a bundle structure.

16. A pacemaker, comprising:
a pulse generator;
a conduction line electrically connected with the pulse generator and comprising a line core and an insulation layer covering the surface of the line core; and
a pacemaker electrode comprising a connecting terminal connected with the conduction line, an electrode line, and a fixing element insertable into a human body for fixing the pacemaker electrode, the electrode line electrically connected with the connecting terminal and the fixing element, the electrode line extending from the connecting terminal to the fixing element, the electrode line comprising:
a body comprising at least one carbon nanotube yarn, the at least one carbon nanotube yarn comprising a plurality of carbon nanotubes interconnected along an axis of the body by van der Waals force; and
an insulation layer covering a surface of the body,
wherein, at least one carbon nanotube yarn is exposed from the insulation layer, the exposed at least one carbon nanotube yarn is a stimulus point and configured to transmit an electrical pulse signal to a target cell or target cells of human body.

17. The pacemaker of claim 16, wherein the plurality of carbon nanotubes extend along an axis of the at least one carbon nanotube yarn.

18. The pacemaker of claim 16, wherein the plurality of carbon nanotubes extend in a spiral along an axis of the at least one carbon nanotube yarn.

19. The pacemaker of claim 16, wherein when there are at least two carbon nanotube yarns, the at least two carbon nanotube yarns are arranged tightly contacting each other in parallel to form a bundle structure.

20. The pacemaker of claim 16, wherein when there are at least two carbon nanotube yarns, the at least two carbon nanotube yarns are wound to form a bundle structure.

* * * * *